United States Patent [19]

Akins

[11] Patent Number: 5,056,875
[45] Date of Patent: Oct. 15, 1991

[54] CONTAINER FOR USE WITHIN A CLEAN ENVIRONMENT

[75] Inventor: Vaughn E. Akins, Austin, Tex.

[73] Assignee: Motorola, Inc., Schaumburg, Ill.

[21] Appl. No.: 325,589

[22] Filed: Mar. 20, 1989

[51] Int. Cl.$^5$ .......................................... A61G 11/00
[52] U.S. Cl. ........................................ 312/1; 222/183; 312/208; 414/217
[58] Field of Search ............... 222/183, 182; 414/217; 312/1, 3, 208

[56] References Cited

U.S. PATENT DOCUMENTS

| | | | |
|---|---|---|---|
| 2,813,022 | 12/1957 | Moulthrop | 2/2 |
| 3,244,329 | 4/1966 | Cates | 222/182 |
| 3,355,230 | 8/1964 | Trexler | 312/1 |
| 3,438,551 | 4/1969 | Belisle | 222/182 |
| 3,439,966 | 12/1965 | Perkins et al. | 312/1 |
| 3,536,370 | 10/1970 | Evans et al. | 312/1 |
| 3,670,718 | 1/1972 | Brendgord | 128/1 |
| 3,713,480 | 1/1973 | Low et al. | 165/46 |
| 3,744,055 | 7/1973 | Brendgord | 2/2 |
| 3,907,389 | 9/1975 | Cox et al. | 312/1 |
| 4,111,753 | 9/1978 | Folsom et al. | 312/1 X |
| 4,302,848 | 12/1981 | Otsuka et al. | 2/2 |
| 4,304,224 | 8/1981 | Fortney | 128/1 |
| 4,532,970 | 8/1985 | Tullis et al. | 141/98 |
| 4,534,389 | 8/1985 | Tullis et al. | 141/98 |
| 4,609,103 | 9/1986 | Bimer et al. | 206/328 |
| 4,634,331 | 1/1987 | Hertel | 414/217 |
| 4,668,153 | 5/1987 | Sperinck et al. | 414/411 |
| 4,674,939 | 6/1987 | Maney et al. | 414/292 |
| 4,676,709 | 6/1987 | Bonora et al. | 414/217 |
| 4,724,874 | 2/1988 | Parikh et al. | 414/217 X |
| 4,746,256 | 5/1988 | Boyle et al. | 414/217 |
| 4,755,010 | 7/1988 | Wilson et al. | 312/208 |
| 4,885,000 | 12/1989 | Hogan | 312/1 X |

Primary Examiner—Kevin P. Shaver
Attorney, Agent, or Firm—John A. Fisher

[57] ABSTRACT

A container is provided for use in a clean environment, thereby allowing functional access to items such as chemicals stored within the container while minimizing contamination to the clean environment. A two-part unitary door includes an access plug and an entry plug. The plugs are separable from one another so that the container may be moved freely within the clean environment while the access plug seals the container from exposure to the clean environment, and the entry plug seals the clean environment from the exterior contaminated area. Structure is provided to enable functional access to the items stored within the container. In other embodiments, containers are provided for such objects as computers, oscilloscopes and the like.

58 Claims, 8 Drawing Sheets

CONTAINER FOR USE WITHIN A CLEAN ENVIRONMENT

TECHNICAL FIELD OF THE INVENTION

This invention pertains in general to clean environments, and more particularly to a container and method for enclosing contaminated objects while allowing functional access to the objects within the clean environment.

BACKGROUND OF THE INVENTION

Clean environments are commonly used in a variety of applications. For example, clean environments, known as "clean rooms", are used in the electronics industry to manufacture and process semiconductor devices. In such semiconductor clean rooms, it is important to maintain a high degree of cleanliness or sterility in order to prevent even small particles from interfering with the fabrication of the extremely small electronic devices. Semiconductor clean rooms are thus continuously being improved to provide ever increasing degrees of sterility in view of the continued miniaturization of the semiconductor devices being fabricated.

Other clean environments are commonly used in the manufacture of pharmaceutical products, wherein it is important to prevent the contamination of the products by contaminants within the air. Other clean environments are used in hospitals, such as clean rooms used for surgery wherein it is important to prevent contamination of open wounds and the like.

In such clean environments, great care is taken to prevent contamination of the clean environment by personnel and objects therein. The personnel are required to be scrupulously clean and to wear protective outer uniforms. Any object brought into the clean environment must be very carefully cleaned before being introduced into the clean environment. Some objects, such as computers, oscilloscopes, and other electronic devices, are difficult to clean. In addition, operation of many electronic devices require the movement of keys on a keyboard, which tends to dislodge particles that may contaminate the sterile atmosphere. Moreover, it is often necessary to calibrate or repair such electronic instruments and it is difficult to perform such calibrations or repair in the clean environment, as contaminated tools must be brought into the environment. Moreover, such calibration or repair often requires opening up the chassis of the electronic instrument, thereby causing additional contamination.

It is also often necessary in the manufacture of semiconductor devices to bring in chemical substances, both liquid and solid, which are used in various fabrication processes. The containers for such chemicals must be cleansed before being brought into the clean environment, which is not only difficult to perform but often does not provide the desired degree of cleanliness.

A need has thus arisen for a technique of allowing contaminated objects to be brought into a clean environment and enabling the objects to be functionally utilized therein without substantially altering the sterility or the cleanliness of the environment. Specifically, a need has arisen for allowing the introduction of electronic devices into a clean environment without the necessity of cleaning the electronic instruments prior to being introduced into the clean room, and yet without contaminating the sterility of the clean environment. A need has further arisen for a technique for introducing chemicals and the like into a clean environment without requiring pre-cleaning of the containers accommodating those chemicals.

SUMMARY OF THE INVENTION

In accordance with the present invention, a container for use within a clean environment is provided which substantially eliminates or prevents disadvantages and problems associated with introducing contaminants into a clean environment.

In accordance with the present invention, a container is located within the clean environment and dimensioned to receive a contaminated object. A communicating port provides communication from the exterior of the clean environment into the container to allow contaminants to be disposed therein without contaminating the clean environment. An operator within the clean environment has functional access to the contaminated object disposed within the container.

More particularly, the present invention permits an operator to manipulate the contaminant disposed within the container. A pump and dispenser allow particulates or fluids stored within the container to be transferred therefrom into the clean environment while minimizing contamination thereto. For contaminated objects with adjustable parameters, such as electronic equipment, a plurality of knobs are provided externally of the container. These knobs communicate with corresponding knobs on the stored device, thereby permitting the operator within the clean environment to adjust the controls of the stored device without exposing said device to the clean environment. A display surface may be provided in a wall of the container to enable viewing of the contaminated object. The invention also contemplates a durable membrane disposed within a wall of the container to allow an operator within the clean environment to communicate with a keyboard disposed in the container. Electrical couplings are also provided such that an operator may have access to input and output terminals on the stored device.

Important technical advantages of the present invention include the ability of an operator within a clean environment to have functional access to a contaminated object while not exposing the object to the clean environment. Therefore, no rigorous cleansing of the contaminated object is necessary prior to its use within the container and its access by an operator within the clean environment. Furthermore, the container and, consequently, the stored contaminated object may be moved freely within the clean environment, thereby allowing the same functional access from any location within that environment.

BRIEF DESCRIPTION OF THE DRAWINGS

Further features and advantages will become more apparent from the following and more particular description of the preferred embodiment of the invention, as illustrated in the accompanying drawings, in which like reference characters generally refer to the same parts of functions throughout the views, and in which.

DETAILED DESCRIPTION OF THE INVENTION

Figure 1:
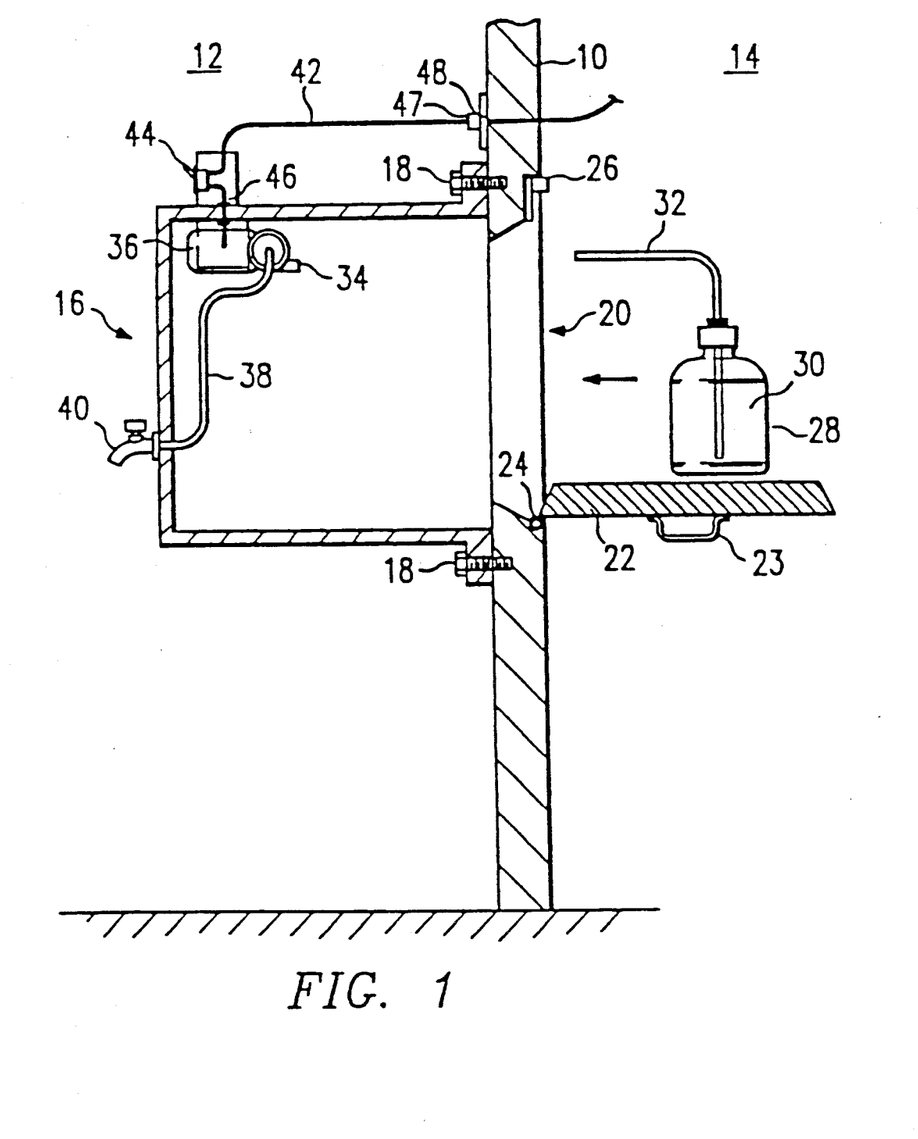
FIG. 1 illustrates a cross-sectional side view of one embodiment of the container of the present invention prior to the storing of a contaminant therein.

FIG. 1 illustrates a cross-sectional view of a first embodiment of the present invention. In FIG. 1, there is shown a dividing wall 10 separating a clean environment 12 from an exterior contaminated or non-sterile area 14. Clean environment 12 may comprise an environment for fabricating semiconductor devices, for conducting medical procedures, or any other of a variety of procedures requiring a clean or sterile atmosphere. Adjacent dividing wall 10 is the container 16 of the present invention. Container 16 may be constructed of any suitable rigid material, such as plastic or the like. Fasteners 18 are used to maintain container 16 in the desired position against dividing wall 10. Fasteners 18 may be bolts, screws, rivets or alternatively may comprise quick release clamps which cooperate with alignment devices to attach container 16 to the desired location on wall 10. O-rings or other sealing devices may be disposed between the container 16 and dividing wall 10 to prevent contamination of clean environment 12.

An entry port 20 is defined through dividing wall 10 so that a contaminated object may be disposed within container 16. A plug or door 22 is pivotally connected to a hinge 24 to seal entry port 20, if desired. A handle 23 is mounted on plug 22 to allow ease in movement thereof. A sliding latch 26 may be moved downward to ensure that plug 22 remains in the closed position.

Figure 2:
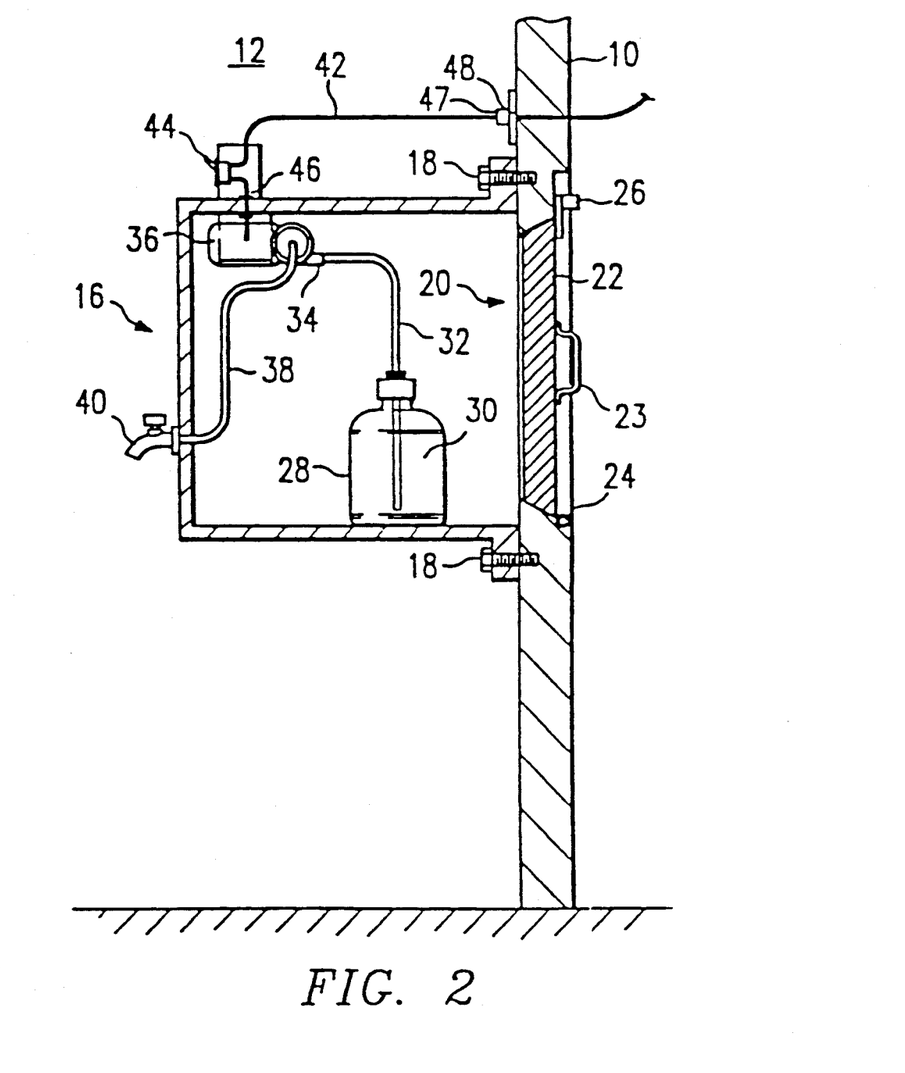
FIG. 2 illustrates a cross-sectional side view of the container of FIG. 1 having a contaminated repository stored therein.

The contaminated object of FIG. 1 comprises a repository or bottle 28 having particulate matter or liquid 30 stored therein. A tube 32 is provided for withdrawing the matter or liquid 30 from repository 28. As shown in FIG. 2, tube 32 can be connected to the inlet 34 of a pump 36, which is coupled by a second tube 38 to an adjustable distributor such as nozzle 40. Nozzle 40 includes a control knob for opening and closing the nozzle to transport the matter 30 from the interior of container 16 to clean environment 12. A power cord 42 is provided to supply electricity to pump 36, and a switch 44 is connected to power cord 42 so that an operator within clean environment 12 can regulate electricity supplied to pump 36. A seal 46 at the intersection of power cord 42 and container 16 prevents contamination from entering the clean environment 12. A plug 47 on the end of power cord 42 is mateable with an electrical outlet 48.

In FIG. 2, repository 28 has been moved from exterior contaminated area 14 through entry port 20 and into container 16. Tube 32 from within repository 28 is attached to inlet 34 of pump 36 so that the matter 30 may be introduced into clean environment 12 through nozzle 40. A person or robotic arm operating from within clean environment 12 can switch on pump 36 and manipulate nozzle 40, thereby obtaining matter 30 without contacting contaminated repository 28. Plug 22 is swung upward by handle 23, thereby closing entry port 20. Sliding latch 26 is then moved downward to maintain plug 22 in the closed position. In this embodiment, sealing of door 22 to dividing wall 10 is not required.

Figure 3:
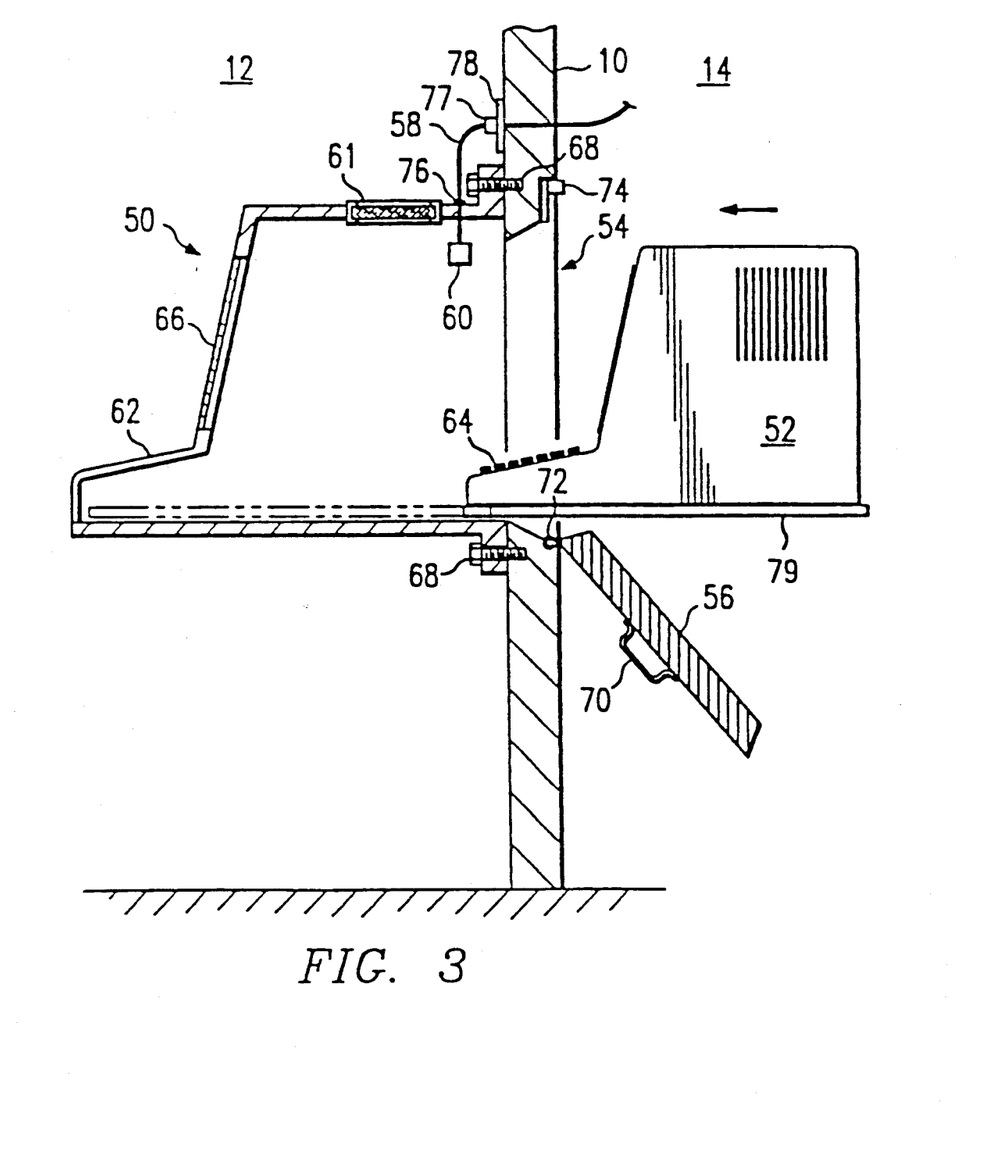
FIG. 3 illustrates a cross-sectional side view of a second embodiment of the container of the present invention wherein said container is shaped to substantially conform to the dimensions of a computer terminal to be stored therein.

FIG. 3 illustrates a cross-sectional view of a second embodiment of the present invention. Again, clean environment 12 is isolated from exterior contaminated area 14 by dividing wall 10. A container 50 is constructed in a shape so as to substantially conform to the exterior shape of an electronic device to be placed therein. For example, the device may comprise a computer terminal 52 which is contaminated with particles which could harm the cleanliness of clean environment 12. An entry port 54 is formed through dividing wall 10 and a corresponding plug or door 56 is hingedly connected to dividing wall 10. Port 54 is of sufficient size to accommodate the passing through of computer terminal 52. A power cord 58 with a female connector 60 at its end provides electricity to computer terminal 52 once disposed within container 50. A filter 61 allows for ventilation of container 50 from clean environment 12. Additional filtered cooling apparatus (not shown) may be attached to filter 61 to withdraw heat created by computer terminal 52.

An interface 62 formed from a suitable flexible membrane allows a person within clean environment 12 to manipulate a keyboard 64 of computer terminal 52. Computer terminal 52 may include a keyboard detached from the monitor and processing unit, and could further include alternative input devices such as a "mouse" or joystick. Container 50 and interface 62 may be modified by one skilled in the art to accommodate such alternative input devices and allow them to be manipulated from outside container 50. A viewing area 66, is disposed within a wall of container 50 for allowing an operator within clean environment 12 to see the contaminated object. Viewing area 66 may be made of glass, plexiglass or other suitable transparent materials.

In a manner similar to the embodiment of FIG. 1, fasteners 68 maintain container 50 against dividing wall 10. Again, a handle 70 allows an operator to pivot plug 56 upward on a hinge 72 to seal entry port 54. A sliding latch 74 may then be moved downward to maintain plug 56 in this closed position. A seal 76 prevents contamination from entering the clean environment 12 where power cord 58 intersects container 50. An electrical plug 77 connected to the end of power cord 58 is mateable with an electrical outlet 78. A slide tray 79 receives terminal 52 and is slidable on ball bearings or the like into and out of container 50.

Figure 4:
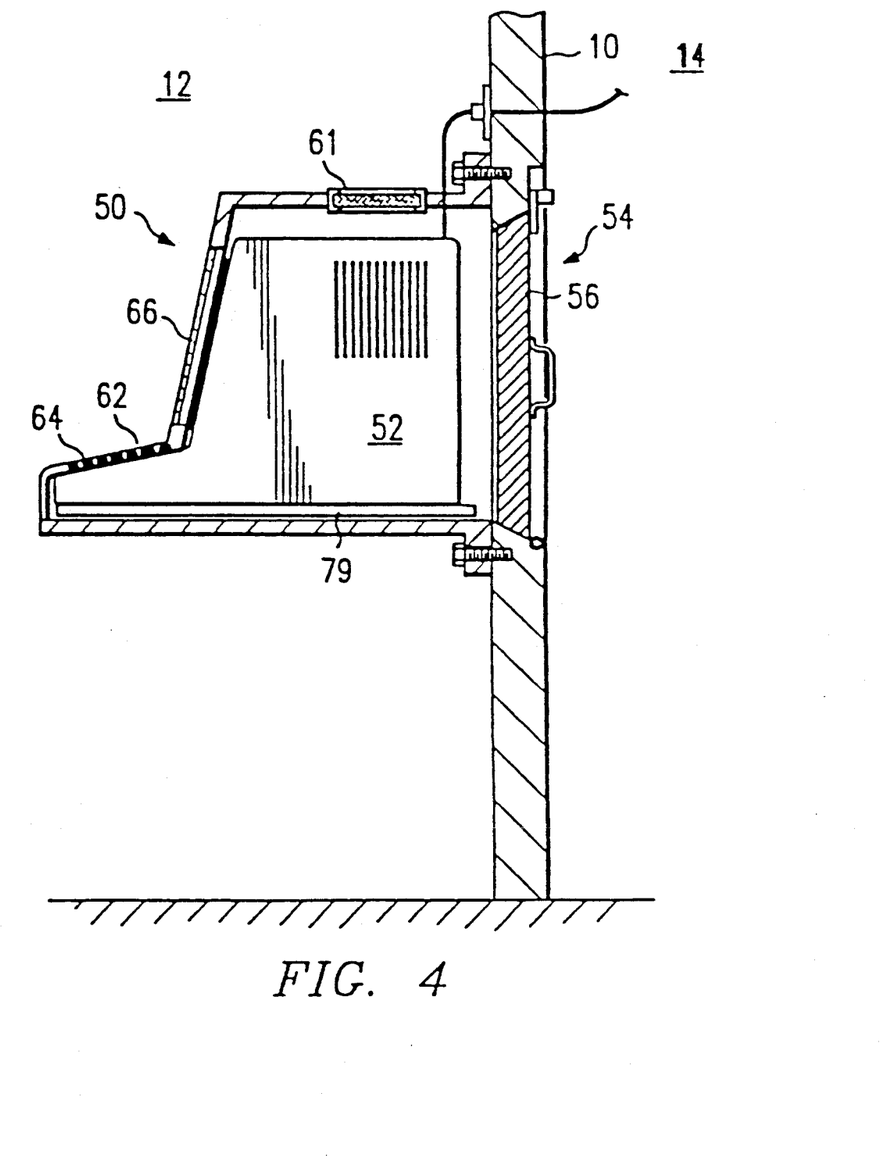
FIG. 4 illustrates a cross-sectional side view of the shaped container of FIG. 3 having a computer terminal stored therein.

FIG. 4 illustrates the container 50 wherein the computer terminal 52 and tray 79 are slid into container 50. Entry port 54 has been sealed by closing plug 56, thereby minimizing environmental disturbance within container 50. The keyboard 64 may be manipulated through the interface 62. Viewing area 66 permits the operator within clean environment 12 to see computer terminal 52 and the visual output from the computer CRT screen. Filter 61 prevents heat emanating from computer terminal 52 from excessively accumulating within container 50.

Figures 5, 6, 6A:
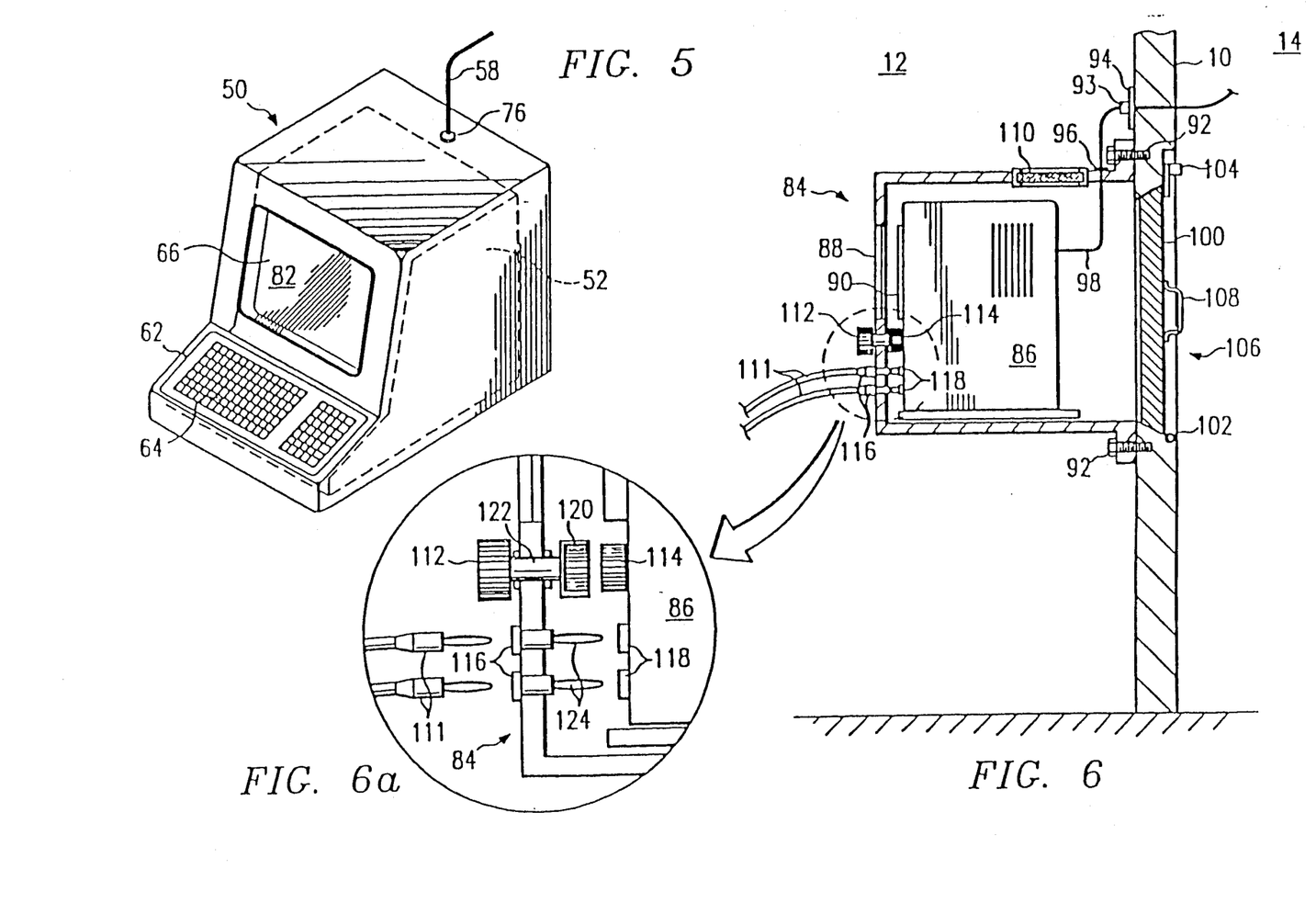
FIG. 5 illustrates a perspective view of the container of FIG. 4 showing the computer terminal stored therein.
FIG. 6 illustrates a cross-sectional side view of a third embodiment of the present invention having a oscilloscope stored therein.
FIG. 6a illustrates an exploded view of the mechanical and electrical interfaces provided with the container of FIG. 6.

FIG. 5 is a perspective view of container 50 of the present invention. As previously noted, container 50 is shaped to substantially conform to the exterior perimeter of at least computer keyboard 64. While keyboard 64 is disclosed, it is to be understood that container 50 could be constructed to substantially conform in shape to other devices disposed therein. As previously described, interface 62 permits an operator within clean environment 12 to manipulate keys on the computer keyboard 64. Interface 62 is shown as a durable plastic membrane, but may alternatively comprise a plurality of mechanical buttons, thereby permitting communication with keyboard 64 or other input devices of computer terminal 52.

It can now be readily appreciated that viewing area 66 permits an operator to see the CRT monitor 82 of computer terminal 52. Viewing area 66 may be adjusted in size to permit viewing more of computer terminal 52 rather than simply monitor 82, or to accommodate different devices stored within container 50. FIG. 5 also illustrates seal 76 used to prevent contamination from entering container 50 where power cord 58 intersects therewith.

It is to be appreciated that as technology advances, the methods of communicating between an operator and a computer terminal will undoubtedly advance. The Applicant fully intends to encompass within the present invention additional modifications which may be constructed as part of the container for allowing communication between an operator or robotic arm and the computer terminal or other electronic device located therein.

FIG. 6 illustrates a third embodiment of the present invention. A container 84 is shown having an oscilloscope 86 disposed therein. The use of oscilloscope 86 is merely exemplary and it is to be understood that numerous other devices beneficial to the activity occurring within clean environment 12 may be placed within container 84. A viewing screen 88 allows an operator within clean environment 12 to view screen 90 of oscilloscope 86.

In a similar manner as FIG. 1, fasteners 92 maintain container 84 against dividing wall 10. A plug 93 is electrically mateable with an outlet 94 defined in dividing wall 10. A seal 96 prevents contamination to clean environment 12 where a power cord 98 intersects container 84. A plug or door 100 pivots about a hinge 102 and a sliding latch 104 may be moved downward to secure plug 100 in the entry port 106. A handle 108 is provided for movement of plug 100. A filter 110 provides for ventilation of the interior of container 84. Electrical signals are provided to oscilloscope 86 via electrical conductors 111.

Another aspect of the invention provides a mechanical interface such that a control knob 112 on the exterior of container 84 communicates with a corresponding knob 114 on oscilloscope 86. Similarly, an electrical interface provides terminals 116 which are externally positioned on container 84 and which are electrically coupled to terminals 118 on oscilloscope 86.

FIG. 6a illustrates in greater detail the construction of the mechanical interface. A female receptacle 120 is provided to frictionally encompass knob 114 on oscilloscope 86. As oscilloscope 86 is pushed into container 84, the knob 114 abut and frictionally engage the interior of receptacle 120, thereby allowing a person or robotic arm within clean environment 12 to adjust knobs 114 by adjusting a correlating control knob 112 disposed on the exterior of container 84. A sealed shaft 122 allows this direct communication.

FIG. 6a further illustrates construction of the electrical interface. The electrical interface includes electrical connectors 124 within the interior of container 84 and corresponding and electrically coupled terminals 116 on the exterior of container 84. Conductors 111 are received by terminals 116. When positioning oscilloscope 86 within container 84, electrical connectors 124 enter terminals 118 existing on oscilloscope 86. These connections will provide electrical signals corresponding to each oscilloscope terminal 118, but accessible from within clean environment 12 by virtue of externally disposed terminals 116. The connection may be by a banana plug as illustrated, or by friction fit, alligator clips, plugs, screws or the like.

Figure 7:
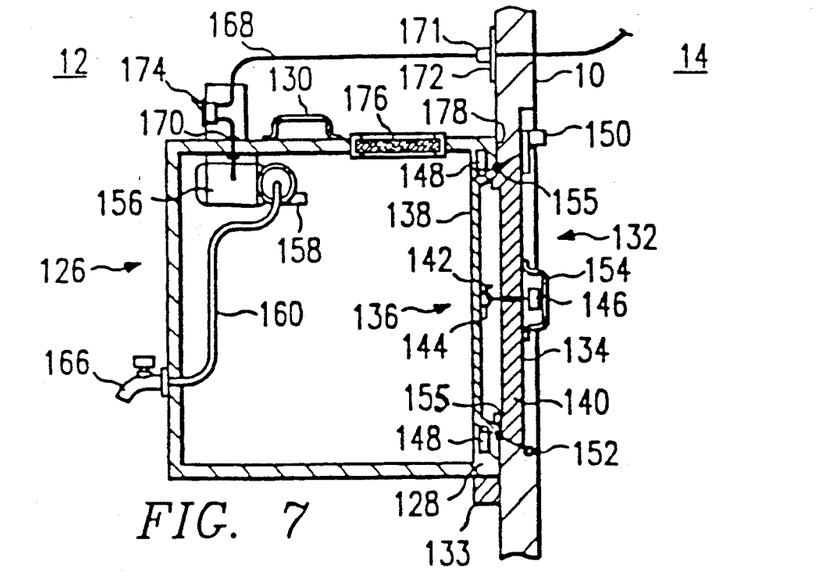
FIG. 7 illustrates a cross-sectional side view of the preferred fourth embodiment of the present invention.

FIG. 7 illustrates the preferred fourth embodiment of container 126 of the present invention. Again, clean environment 12 is shown separated from contaminated exterior area 14 by dividing wall 10. Although container 126 is shown adjacent dividing wall 10, a back wall 128 is constructed for container 126 so that it may be disengaged from dividing wall 10 and moved freely within clean environment 12 while enclosing any contaminants encompassed therein. Container 126 can be carried and manually supported by an overhead handle 130. An entry port 132 formed within dividing wall 10 permits communication with the interior of container 126 from contaminated exterior area 14. The detachment of container 126 from dividing wall 10 could potentially expose clean environment 12 to contaminated exterior area 14 by virtue of entry port 132. Therefore, a twopiece unitary door 134 is provided for sealing entry port 132, thereby preventing such an occurrence.

Due to the separately constructed back wall 128 of container 126, there is also formed an access port 136 therein for communication with entry port 132. A block or guide 133 may be placed on dividing wall 10 to enable ports 132 and 136 to be accurately mated. The two-piece unitary door 134 is constructed to coincidingly plug both access port 136 of container 126 and entry port 132 of dividing wall 10. Thus, unitary door 134 comprises both an access plug 138 and an entry plug 140. A hook 142 and eyelet 144 can be connected so that plugs 138 and 140 remain in contact with one another while container 126 abuts with dividing wall 10. As will be subsequently described, hook 142 and eyelet 144 will be disengaged by turning an attachment knob 146 before moving container 126 away from dividing wall 10. In so doing, access plug 138 will remain within access port 136, while entry plug 140 will remain within entry port 132. As such, entry port 132 of dividing wall 10 will be sealed, as will access port 136 of container 126.

Therefore, any contaminants within container 126 remain isolated from clean environment 12, and clean environment 12 remains isolated from contaminated exterior area 14. Spring-loaded pins 148 insure that access plug 138 remains within access port 136. A sliding latch 150 in combination with a hinge 152 maintain entry plug 140 within entry port 132. A handle 154 may be used to position unitary door 134. An O-ring 155 is situated around the perimeter of unitary door 134 where access plug 136 and entry plug 138 form a union.

Various adjustable distributors, control knobs and electrical conductors may be provided with container 126 as described with reference to the alternative embodiments in FIGS. 1-6. For example, in FIG. 7 there is shown, as was discussed in reference to FIG. 1, dispensing apparatus. This includes a pump 156 having an inlet 158 and a dispensing tube 160 for transporting matter 162 from a repository 164 (see FIG. 8) to an adjustable nozzle or distributor 166. Pump 156 receives electricity from a power cord 168 which has a seal 170 where it intersects container 126. A plug 171 on the end of power cord 168 is mateable with an electrical outlet 172. Further included is a switch 174 along power cord 168 for regulating electricity to container 126. A filter 176 allows air to ventilate from container 126 into clean environment 12. As will be shown, container 126 may be freely moved within clean environment 12 while allowing operators therein the ability to manipulate either substances or devices enclosed within container 126.

FIG. 7 further illustrates the interfacing area 178 between back wall 128 of container 126 and dividing wall 10. The two-piece unitary door 134 may be swung open and shut by virtue of hinge 152 toward the exterior side of dividing wall 10. Sliding latch 150 can slide vertically to hold unitary door 134 in a closed position. While hinge 152 and sliding latch 150 are disclosed, it should be understood that no retaining structure is necessary, and thus unitary door 134 could also serve its purpose being completely detached from dividing wall 10.

Seals, such as O-ring 155, are placed around the outer perimeter of the unitary door where access plug 138 and entry plug 140 mate to form a junction. O-ring 155 minimizes contamination of clean environment 12, both when unitary door 134 is removed, and once it is in place and container 126 is being moved within clean environment 12. While hook 142 and eyelet 144 are disclosed as a detaching device for maintaining contact between access plug 138 and entry plug 140, it is to be understood that numerous alternatives exist to maintain the two plugs in contact with one another during the necessary time intervals.

Figure 8:
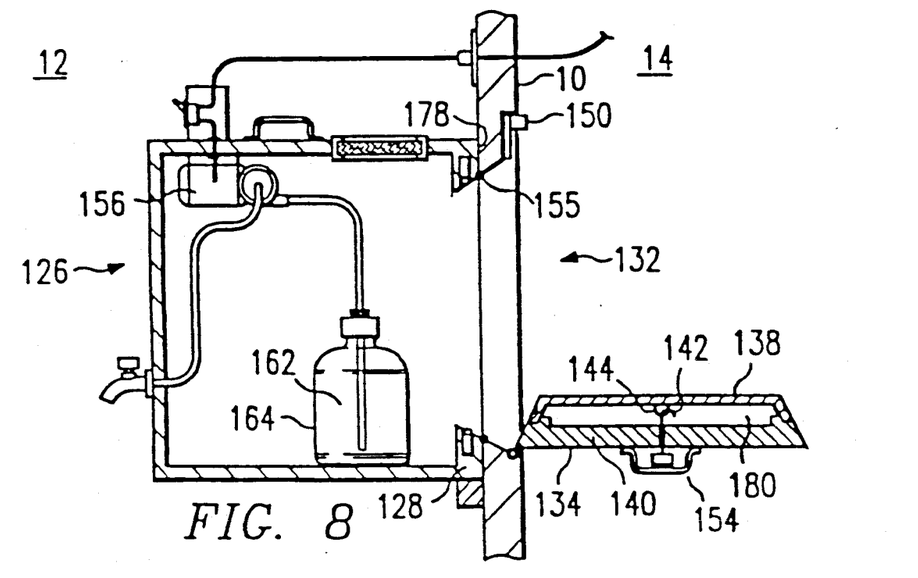
FIG. 8 illustrates a cross-sectional side view of the container of FIG. 7 having a contaminated repository placed therein.

FIG. 8 illustrates unitary door 134 in an opened position, such that access is allowed to the interior of container 126 from exterior contaminated area 14. Sliding latch 150 is temporarily slid above entry port 132 so that unitary door 134 may be pivoted open. It may readily be seen that in this opened position, O-ring 155 is helpful in preventing contaminated air from seeping between interfacing area 178 of container back wall 128 and dividing wall 10. With unitary door 134 in the opened position, it is important that hook 142 and eyelet 144 maintain access plug 138 and entry plug 140 against one another. This assures, as is necessary, that clean air is trapped in the area 180 between those two plugs. As will become apparent in FIG. 10, maintained area 180 of clean air is necessary to minimize contamination to clean environment 12.

As shown in FIG. 8, repository 164 is inserted into container 126 through the opened ports. Suitable tubes are inserted from repository 164 to pump 156 as previously noted.

Figure 9:
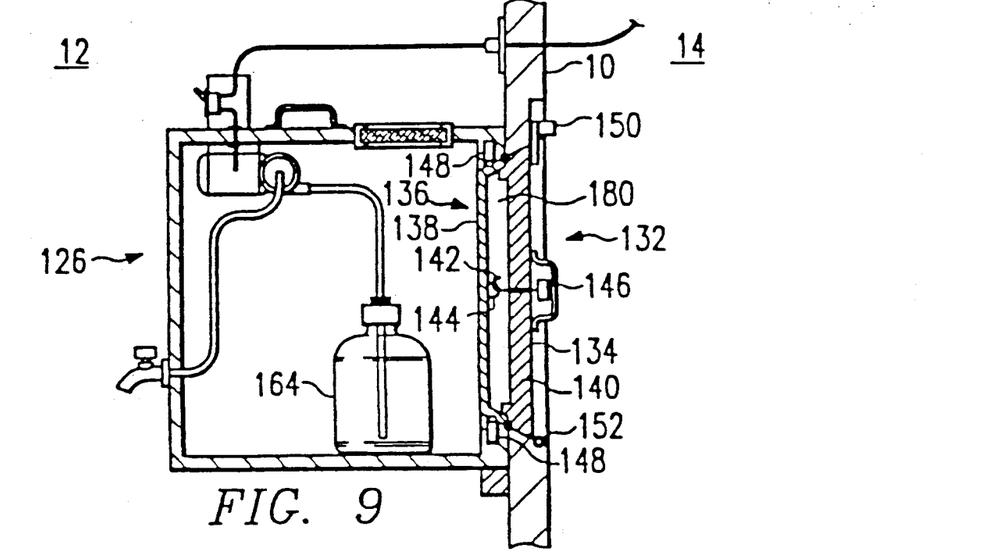
FIG. 9 illustrates a cross-sectional side view of the container of FIG. 8 after sealing of the container.

FIG. 9 illustrates container 126 of the present invention after a repository 164 has been enclosed therein, and unitary door 134 is pivoted back to close ports 132 and 136. Sliding latch 150 has been moved downward to maintain unitary door 134 in that position. The interior of container 126 is thus sealed. By turning attachment knob 146, hook 142 may now be disengaged from eyelet 144, thereby freeing access plug 138 from entry plug 140.

Figure 10:
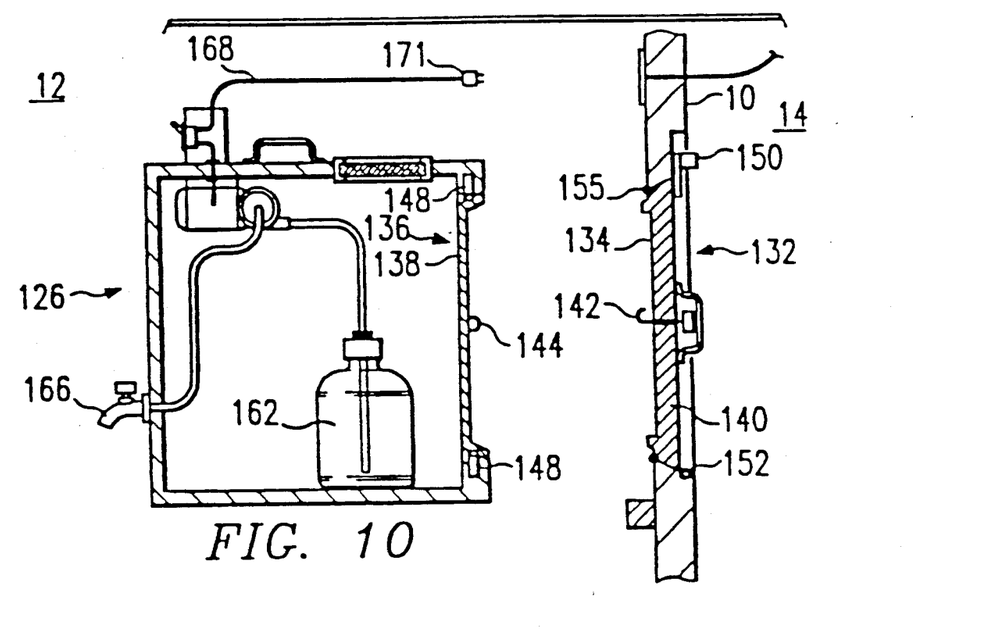
FIG. 10 illustrates a cross-sectional side view of the container of FIG. 8 after having been disengaged from the wall of the clean environment.

As shown in FIG. 10, container 126 may then be moved away from dividing wall 10 and access and entry plugs 138 and 140 will thereafter remain in respective ports 136 and 132. Spring-loaded pins 148 retain access plug 138 within access port 136, so that plug 138 remains with container 126 to maintain the sealing thereof. The combination of hinge 152 and sliding latch 150 retain entry plug 140 within entry port 132, in order to seal clean environment 12 from external contaminated area 14.

FIG. 10 illustrates how hook 142 and eyelet 144 are disengaged to allow free movement of container 126 while preserving access plug 138 within access port 136. It can now be appreciated that area 180 (see FIG. 8) previously trapped between access plug 138 and entry plug 140 has now been exposed to the interior of clean environment 12. As mentioned above, area 180 has been maintained in a clean fashion, and therefore the exposure thereof to clean environment 12 has little contaminating effect thereto. Power cord 168 may be of sufficient length to allow movement of container 126 and dispensing of material 162 within clean environment 12. Alternatively, plug 171 disposed on the end of power cord 168 may be unplugged for accessing electrical outlets provided within clean environment 12. O-ring 155 prevents contamination to the clean environment 12 when entry port 132 is sealed thereby, and container 126 is removed from dividing wall 10.

Figure 11:
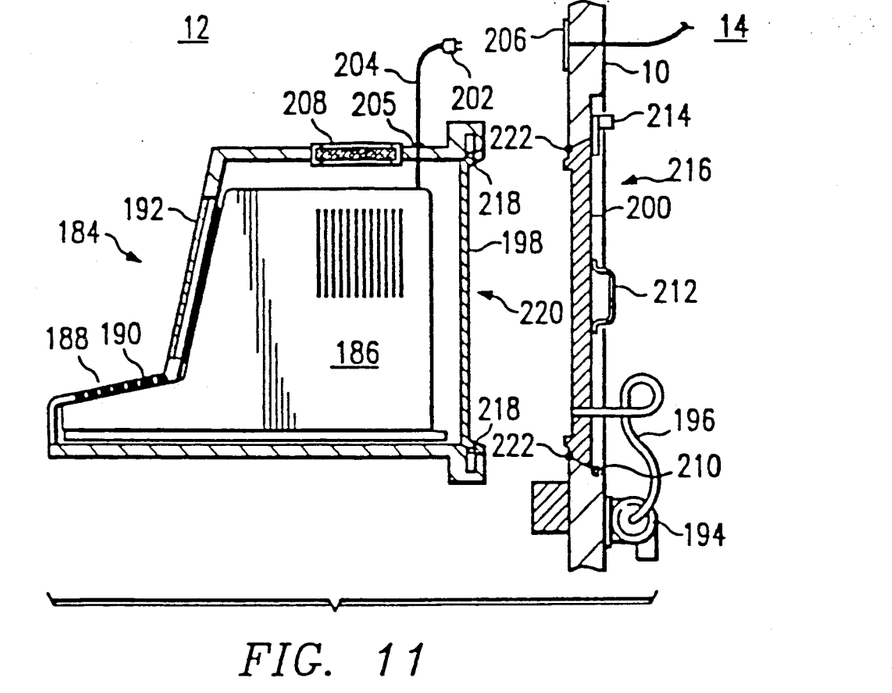
FIG. 11 illustrates a fifth embodiment of the present invention having a computer terminal stored therein and detached from the clean environment wall.

FIG. 11 illustrates a fifth embodiment of the present invention. A container 184 is constructed such that its perimeter will substantially conform in shape to a computer terminal 186. An interface 188, mateable with a computer keyboard 190, permits an operator within clean environment 12 to have functional access to keyboard 190. A viewing area 192 disposed within a wall of container 184 permits an operator to view output provided by computer terminal 186. A vacuum pump 194 having a tube 196 connected thereto permits an area of low pressure to be created between access plug 198 and entry plug 200 when the two plugs 198 and 200 are in contact with one another. Vacuum pump 194 can further be utilized to maintain the sterility of the area 180 (see FIG. 8) between plugs 198 and 200 which is critical as discussed above.

Similar to the discussion in connection with container 126 of FIG. 10, the container 184 illustrated in FIG. 11 may be removed from dividing wall 10 without contaminating clean environment 12. An electrical plug 202 is disposed on the end of a power cord 204 and plugged into an outlet 206 on dividing wall 10. Plug 202 may be disconnected from outlet 206 and plugged into alternative outlets within clean environment 12. A seal 205 prevents contamination of clean environment 12 where power cord 204 enters container 184. A filter 208 permits ventilation of the interior of container 184 into clean environment 12.

Similar to the discussion with reference to FIG. 7, there are numerous components illustrated in FIG. 11 for accessing and enclosing the interior of particularly shaped container 184 prior to the removal thereof from dividing wall 10. Entry plug 200, by virtue of the vacuum created by vacuum pump 194, will be in contact with access plug 198. The combined plugs pivot on a hinge 210 connected to dividing wall 10. A handle 212 permits ease in swinging connected plugs 198 and 200. A sliding latch 214 maintains entry plug 200 within the entry port 216. Spring-loaded pins 218 maintain access plug 198 within access port 220 once particularly shaped container 184 is removed from dividing wall 10. An O-ring 222 seals clean environment 12 from exterior contaminated area 14, both during accessing the interior of particularly shaped container 184 and once the same has been removed from dividing wall 10.

The interior of container 184 is accessed while container 184 is adjacent dividing wall 10. Vacuum pump 194 is turned on, thereby creating a suction through vacuum tube 196. Vacuum tube 196 communicates with the area between access plug 198 and entry plug 200, and therefore a low pressure is created within that area. The low pressure will maintain access plug 198 and entry plug 200 in contact with one another, and will further remove contaminant particles trapped between plugs 198 and 200. Sliding latch 214 is then moved upward, and the coupled plugs are then pivoted downward by an operator pulling on handle 212. Computer terminal 186 may then be disposed within container 184. Vacuum pump 194 remains on during this process to ensure that plugs 198 and 200 remain in contact with one another.

After computer terminal 186 is placed within container 184, combined plugs 198 and 200 are pivoted upward, thereby sealing entry port 216 and access port 220. Sliding latch 214 is moved downward to maintain plugs 198 and 200 in this closed position. Vacuum pump 194 is then turned off, thereby ending the low pressure upward, thereby sealing entry port 216 and access port 220. Sliding latch 214 is moved downward to maintain plugs 198 and 200 in this closed position. Vacuum pump 194 is then turned off, thereby ending the low pressure attraction between access plug 198 and entry plug 200. Container 184 may then be removed from dividing wall 10 and moved freely within clean environment 12.

It may thus be seen that there are numerous structures and techniques for providing the separable two-part plug or door functions required by the present invention. Another example of a structure for providing this function comprises a relatively stiff membrane which provides the function of the entry plug 200, in combination with the access plug 198. In this configuration, a lever or the like is attached to the center area of the membrane and operation of the lever causes the membrane to be pulled away from contact with access plug 198, thus causing a vacuum to exist between plugs 198 and 200. The lever is locked into position to maintain pressure on the membrane as the membrane and the plug are moved away from ports 216 and 220, thereby maintaining the vacuum and maintaining the two devices as a unit. Good seals are provided between the membrane and the plug to maintain the vacuum therebetween. When it is desired to separate the membrane from the plug, the lever would be unlocked from its position and the membrane is allowed to return to its normal nondeformed state. This eliminates the distance between the membrane and the plug, dissipating the vacuum and allowing the membrane and the plug to be separated. Other devices for joining and separating the plugs will be understood by one skilled in the art.

Figure 12:
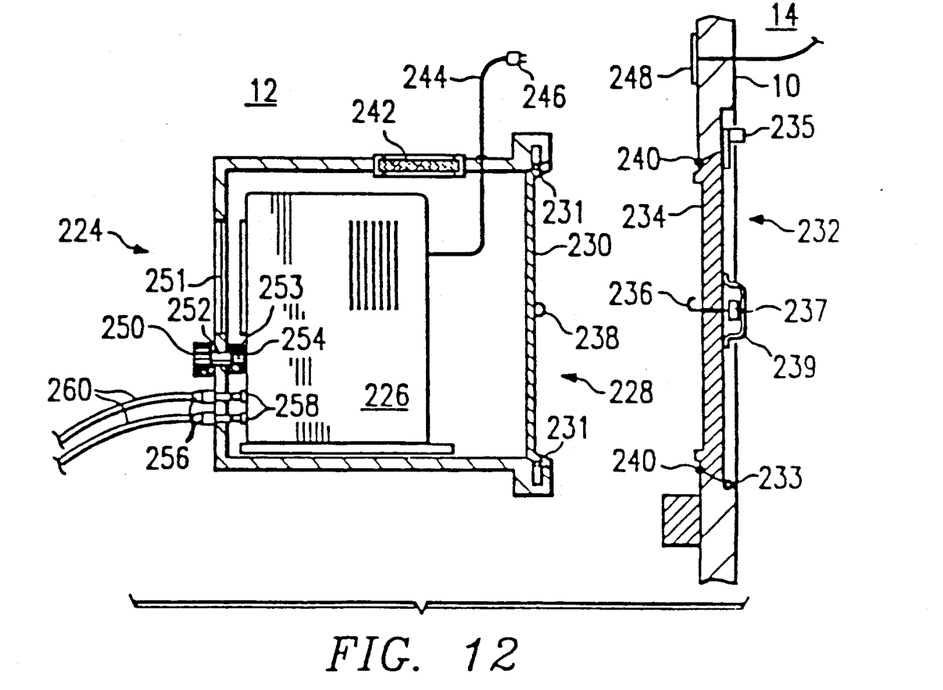
FIG. 12 illustrates a sixth embodiment of the present invention having a oscilloscope stored therein and detached from the clean environment wall.

FIG. 12 illustrates a sixth embodiment of the present invention. A container 224 is constructed to accommodate an electronic device such as an oscilloscope 226. Similar to the discussion in reference to FIGS. 7 and 11, components are included for mating the container 224 against dividing wall 10 while having access to the interior of container 224. Further, elements are included to permit removal of container 224 from dividing wall 10 while minimizing contamination to clean environment 12.

An access port 228 is formed in container 224 for accessing the interior thereof. A corresponding access plug 230 seals access port 228 to prevent contamination to clean environment 12. Spring-loaded pins 231 further maintain access plug 230 within access port 228. Dividing wall 10 has constructed therein an entry port 232 which communicates with access port 228. Entry plug 234 is mateable with access plug 230, and further seals entry port 232. A hinge 233 connects entry plug 234 to dividing wall 10. A sliding latch 235 is moveable against entry plug 234. A hook 236, disposed through entry plug 234, is adjustable via a knob 237 to connect to an eyelet 238. Eyelet 238 is attached to access plug 230. A handle 239 is fastened to entry plug 234. An O-ring 240 is placed where access plug 230 and entry plug 234 form a junction.

Numerous devices are associated with container 224 to accommodate enclosed oscilloscope 226. A filter 242 permits ventilation of container 224 into clean environment 12. A power cord 244 having a plug 246 at one end permits the coupling of the oscilliscope to a source of electrical power. Electrical and mechanical couplings 256, 260, and 250, 252 permit the operator within clean environment 12 to have electrical access to input/output signals of oscilloscope 226.

Although the present invention has been described and illustrated with reference to specific embodiments thereof, it is not intended to limit the invention to these illustrative embodiments. It should be understood that various changes, substitutions and alterations can be made hereto without departing from the spirit and scope of the invention as defined by the appended claims.

What is claimed is:

1. Apparatus for minimizing contamination of a clean environment comprising:
    a container located within the clean environment and dimensioned t receive a contaminated object;
    structure for communicating from the exterior of the clean environment into the interior of said container in order to allow the contaminated object to be inserted into said container without contaminating the clean environment; and
    means associated with said container for enabling functional access to the contaminated object from within the clean environment, without contaminating the clean environment.

2. The apparatus of claim 1 wherein said means for enabling functional access comprises a dispenser for allowing substance contained within the contaminated object to be dispensed through said container into the clean environment with minimum contamination to the clean environment.

3. The apparatus of claim 2 wherein said dispenser comprises:
an adjustable distributor disposed on the external side of said container and extending into the container; and
means for transporting the substance from the contaminated object to said distributor.

4. The apparatus of claim 1 wherein said means for enabling functional access comprises structure for allowing physical manipulation of the contaminated object externally of said container while minimizing the contamination to the clean environment.

5. The apparatus of claim 1 wherein the contaminated object comprises an electronic device, said means for enabling functional access allowing the electronic device to be manipulated and operated by an operator within the clean environment while minimizing the contamination to the clean environment.

6. The apparatus of claim 5 wherein said means for enabling functional access comprises manipulation means actuatable by the operator in order to actuate controls of the electronic device.

7. The apparatus of claim 5 wherein said manipulation means comprises a membrane for communicating with a keyboard of the contaminated object.

8. The apparatus of claim 5 and further including a display on said container for viewing the contaminated object.

9. The apparatus of claim 5 wherein the electronic device further includes electrical terminals, said means for enabling functional access further including structure associated with said container for accessing the electrical terminals.

10. The apparatus of claim 6 wherein said manipulation means comprises a control knob disposed on an external side of said container, said control knob communicating with a receptacle disposed within said container for receiving and controlling adjustable knobs on the contaminated object.

11. The apparatus of claim 10 wherein said receptacle frictionally fits over the adjustable knobs on the contaminated object.

12. The apparatus of claim 10 wherein said control knob communicates with said receptacle by a sealed shaft through said container, said control knob being fitted on said shaft to enable a received adjustable knob on the electronic device to be moved.

13. The apparatus of claim 1 wherein the contaminated object comprises an electronic device having a keyboard and a display, said container being shaped to receive the electronic device, and having manipulating means mating with the keyboard to allow operation of the keyboard.

14. The apparatus of claim 13 and further including viewing means which allows viewing of the display of the electronic device.

15. Apparatus for minimizing contamination of a clean environment comprising:
a container located within the clean environment and dimensioned to receive a contaminated object;
structure for communicating from the exterior of the clean environment into the interior of said container in order to allow the contaminated object to be placed inside the container; and
means for sealing said container independently from the clean environment after the contaminated object is disposed within said container, such that said container may be moved freely within the clean environment while minimizing contamination to the clean environment.

16. The apparatus of claim 15 and further comprising means associated with said container for enabling functional access to the contaminated object within said container.

17. The apparatus of claim 16 wherein said means for enabling functional access comprises a dispenser for allowing substance contained within the contaminated object to be dispensed through said container into the clean environment with minimum contamination to the clean environment.

18. The apparatus of claim 17 wherein said dispenser comprises:
an adjustable distributor disposed on the external side of said container and extending into said container; and
means for transporting the substance from the contaminated object to said distributor.

19. The apparatus of claim 16 wherein said means for enabling functional access comprises structure for allowing physical manipulation of the contaminated object externally of said container while minimizing the contamination to the clean environment.

20. The apparatus of claim 16 wherein the contaminated object comprises an electronic device, said means for enabling functional access allowing the electronic device to be manipulated and operated by an operator within the clean environment while minimizing the contamination to the clean environment.

21. The apparatus of claim 20 wherein said means for enabling functional access comprises manipulation means actuatable by the operator in order to actuate controls of the electronic device.

22. The apparatus of claim 20 wherein said manipulation means comprises a membrane for communicating with a keyboard of the contaminated object.

23. The apparatus of claim 20 and further including viewing means on said container for viewing the contaminated object.

24. The apparatus of claim 20 wherein the electronic device further includes electrical terminals, said means for enabling functional access further including structure associated with said container for accessing the electrical terminals.

25. The apparatus of claim 21 wherein said manipulation means comprises a control knob disposed on an external side of said container, said control knob communicating with a receptacle disposed within said container for receiving and controlling adjustable knobs on the contaminated object.

26. The apparatus of claim 25 wherein said receptacle frictionally fits over the adjustable knobs on the contaminated object.

27. The apparatus of claim 25 wherein said control knob communicates with said receptacle by a sealed shaft through said container, said control knob being fitted on said shaft to enable a received adjustable knob on the electronic device to be moved.

28. The apparatus of claim 15 wherein the contaminated object comprises an electronic device having a keyboard and a display, said container being shaped to receive the electronic device, and having manipulating means mating with the keyboard to allow operation of the keyboard from within the clean environment.

29. The apparatus of claim 28 and further including viewing means for viewing the display of the electronic device.

30. The apparatus of claim 15 and further including a pump for pumping substance contained within the contaminated object to the clean environment.

31. Apparatus for maintaining the cleanliness of a clean environment having a entry port comprising:
a container for being disposed in the clean environment and dimensioned to receive a contaminated object having functions necessary within the clean environment, the exterior of the container being clean and shielded from the interior of said container;
said container having structure which enables functional access to the contaminated object;
an access port formed in said container and operable to mate with the entry port of the clean environment in order to allow the contaminated object to be inserted through the entry port and said access port to the interior of said container; and
port sealing structure operable to seal the entry port and said access port, said sealing structure separable into two parts, each part engageable with one of said ports in order to separately seal the clean environment and said container, so that said container may be moved within the clean environment while protecting the cleanliness thereof.

32. The apparatus of claim 31 wherein said port sealing structure comprises:
a first part engageable with said access port to seal said container, said first part having a clean surface which is maintained away from contamination; and
a second part engageable with the entry port in order to seal the clean environment from contamination, said second part having a clean surface maintained away from contamination.

33. The apparatus of claim 32 wherein said first and second parts are engageable as a unit with said clean surfaces disposed adjacent one another.

34. The apparatus of claim 31 and further including interface sealing means at a junction formed by the mating of the entry port with said access port so that the clean environment remains substantially free from contamination when said ports are mated and said port sealing structure is removed from the entry port.

35. The apparatus of claim 31 wherein said structure which enables functional access comprises a dispenser for allowing substance contained within the contaminated object to be dispensed through said container into the clean environment with minimum contamination to the clean environment.

36. The apparatus of claim 31 wherein said structure which enables functional access comprises structure for allowing physical manipulation of the contaminated object externally of said container while minimizing the contamination to the clean environment.

37. The apparatus of claim 31 wherein the contaminated object comprises an electronic device, said structure which enables functional access allowing the electronic device to be manipulated and operated by an operator within the clean environment while minimizing the contamination to the clean environment.

38. Apparatus for minimizing contamination of a clean environment having an entry port, comprising:
a container having an access port, mateable with the entry port;
an access plug for sealing said access port and an entry plug for sealing the entry port, said access plug and said entry plug joinable to form a unitary door;
said unitary door removable as a unit to open said ports to enable access to the interior of said container to allow insertion of a contaminated object through the opened mated ports into the container;
said unitary door being insertable into said mated ports;
means for disengaging said plugs of said unitary door to enable said container to be freely moveable within the clean environment;
said access plug sealing said access port and said entry plug sealing the entry port; and
means associated with said container for enabling functional access to the contaminated object from within the clean environment, without contaminating the clean environment.

39. The apparatus of claim 38 wherein said plugs are joined by a detachable device which may be selectively operated in order to separate said plugs.

40. The apparatus of claim 39 wherein said detachable device comprises a mechanical latch.

41. The apparatus of claim 39 wherein said detachable device comprises means for creating a reduced pressure between said entry plug and said access plug to force said plugs in contact with one another.

42. The apparatus of claim 38 and further comprising a hinge for pivoting said unitary door away from and into said ports.

43. The apparatus of claim 38 wherein said means for enabling functional access comprises a dispenser for allowing substance contained within the contaminated object to be dispensed through said container into the clean environment with minimum contamination to the clean environment.

44. The apparatus of claim 38 wherein said means for enabling functional access comprises structure for allowing physical manipulation of the contaminated object externally of said container while minimizing the contamination to the clean environment.

45. The apparatus of claim 38 wherein the contaminated object comprises an electronic device, said means for enabling functional access allowing the electronic device to be manipulated and operated by an operator within the clean environment while minimizing the contamination to the clean environment.

46. A method of minimizing contamination to a clean environment having a container disposed therein, comprising:
accessing the interior of the container while preventing contamination of the clean environment;
introducing a contaminated object into the interior of the container while preventing contamination of the clean environment; and
enabling functional access to the contaminated object in the clean environment.

47. The method of claim 46 and further including sealing the container independently of the clean environment, such that the contaminated object introduced into the interior of the container does not substantially contaminate the clean environment while the container is moved within the clean environment.

48. The method of claim 46 and further comprising manipulating the contaminated object externally of the container while minimizing the contamination to the clean environment.

49. The method of claim 48 wherein the contaminated object contains a substance, and said manipulating step further includes transporting the substance through the container into the clean environment while minimizing the contamination to the clean environment.

50. The method of claim 48 wherein the contaminated object is an electronic device having terminals, and said manipulating step includes electrically accessing the terminals of the electronic device.

51. The method of claim 48 wherein said manipulating step further includes adjusting changeable controls on the contaminated object externally of the container, and viewing through the container data generated by the contaminated object.

52. A method of reducing contamination of a clean environment, comprising:
 maintaining the exterior of a container within the environment substantially free of contamination;
 accessing the interior of the container while preventing substantial contamination of the clean environmental;
 sealing the container independently of the clean environment such that the contaminated object introduced into the interior of the container does not substantially contaminate the clean environment;
 moving the container freely within the clean environment; and
 enabling functional access to the contaminated object by an operator in the clean environment.

53. The method of claim 52 and further comprising:
 dispensing material within the contaminated object through the container into the clean environment while preventing substantial contamination of the clean environment.

54. The method of claim 52 wherein the contaminated object is an electronic device having controls, and said enabling step further comprises physically moving the controls externally of the container while minimizing contamination to the clean environment.

55. The method of claim 54 and further comprising viewing data generated by the electronic device.

56. A method of minimizing contamination of a clean environment having a container disposed therein, the clean environment having an entry port, and the container having an access port, comprising:
 matching the access port adjacent the entry port, the access port having a corresponding access plug and the entry port having a corresponding entry plug such that said access plug and said entry plug abut to form a two-part unitary door to aid matched ports;
 removing said two-part unitary door as a unit to open the ports thereby accessing the interior of the container;
 inserting a contaminated object through said opened ports into said container;
 replacing said two-part unitary door within said ports;
 disengaging said plugs of said two-part unitary door such that said access plug obstructs the access port while said entry plug obstructs the entry port;
 disengaging the container to separate the ports while maintaining said access plug in the access port and maintaining said entry plug in the entry port; and
 enabling functional access to the contaminated object by an operator in the clean environment.

57. The method of claim 56 and further comprising:
 dispensing material within the contaminated object through the container into the clean environment while preventing substantial contamination of the clean environment.

58. The method of claim 56 wherein the contaminated object is an electronic device having controls, and said enabling step further comprises physically moving the controls externally of the container while minimizing contamination to the clean environment.

* * * * *

UNITED STATES PATENT AND TRADEMARK OFFICE
CERTIFICATE OF CORRECTION

PATENT NO. : 5,056,875

DATED : October 15, 1991

INVENTOR(S) : Vaughn Edward Akins

It is certified that error appears in the above-identified patent and that said Letters Patent is hereby corrected as shown below:

Column 10, Line 55, change "t" to --to--.

Signed and Sealed this

Twenty-third Day of February, 1993

Attest:

STEPHEN G. KUNIN

*Attesting Officer*     Acting Commissioner of Patents and Trademarks